United States Patent [19]

Ishihara et al.

[11] Patent Number: 4,568,771

[45] Date of Patent: Feb. 4, 1986

[54] METHOD FOR STABILIZING ALIPHATIC HIGHER ALDEHYDE COMPOUNDS

[75] Inventors: Toshinobu Ishihara; Akira Yamamoto; Mitsuyoshi Ohshima; Nobolu Aiba, all of Niigata, Japan

[73] Assignee: Shin-Etsu Chemical Co., Ltd., Tokyo, Japan

[21] Appl. No.: 570,351

[22] Filed: Jan. 13, 1984

[51] Int. Cl.$^4$ ............................................. C07C 45/86
[52] U.S. Cl. .................................... 568/421; 568/448
[58] Field of Search ............................. 568/421, 448

[56] References Cited

U.S. PATENT DOCUMENTS

| | | | |
|---|---|---|---|
| 1,550,869 | 8/1925 | Bogin | 568/421 |
| 2,886,493 | 5/1959 | Mecorney et al. | 568/421 X |
| 4,414,419 | 11/1983 | Weber et al. | 568/421 |

FOREIGN PATENT DOCUMENTS

| | | |
|---|---|---|
| 47-32963 | 8/1972 | Japan . |
| 790380 | 2/1958 | United Kingdom . |
| 2042536 | 9/1980 | United Kingdom . |
| 539023 | 12/1976 | U.S.S.R. . |

Primary Examiner—Natalie Trousof
Assistant Examiner—Vera C. Clarke
Attorney, Agent, or Firm—Toren, McGeady, Stanger, Goldberg & Kiel

[57] ABSTRACT

Aliphatic higher aldehyde compounds, e.g. Z-11-hexadecenal and Z-9-tetradecenal, can be stabilized against oxidation to form a carboxylic acid and trimer formation by the addition of a stabilizer compound including a tertiary amine compound, benzophenone compound, salicylate compound, benzotriazole compound and cyanoacrylate compound together with or without further admixture of an antioxidant.

7 Claims, No Drawings

METHOD FOR STABILIZING ALIPHATIC HIGHER ALDEHYDE COMPOUNDS

BACKGROUND OF THE INVENTION

The present invention relates to a method for stabilizing an aliphatic higher aldehyde compound or, more particularly, to a method for stabilizing an aliphatic higher aldehyde compound during prolonged storage by remarkably reducing the formation of oxidation products of the aldehyde such as carboxylic acids and trimers of the aldehyde.

As is well known, aliphatic higher aldehyde compounds are usually unstable when prolongedly stored under atmospheric conditions. The reactions mainly responsible to the instability of the aldehyde compounds are, for example, (1) the autoxidation of the aldehyde to form a corresponding carboxylic acid according to the reaction equation

$$R-CHO + O \rightarrow R-CO-OH, \qquad (I)$$

in which the symbol R denotes an aliphatic hydrocarbon group, and (2) the formation of a trimer according to the reaction equation

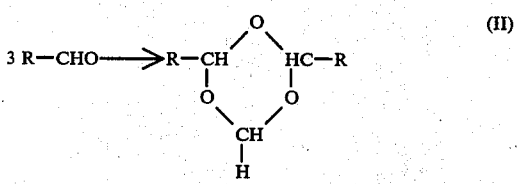

in which R has the same meaning as defined above.

It is conventionally practiced to add an antioxidant to an aliphatic higher aldehyde compound with an object to increase the stability thereof in storage. This method of adding an antioxidant is, however, not quite effective to reduce the rate of the carboxylic acid formation since the reaction of the above given equation (I) proceeds autocatalytically by the carboxylic acid per se or is accelerated by ultraviolet light. The method of the antioxidant addition is much less effective when the reaction of the trimer formation is concerned.

The above described problem of the instability of aliphatic higher aldehyde compounds is particularly important in the newly developed method of pest or noxious insect control by use of a sex pheromone compound, which sometimes belongs to a class of aliphatic higher aldehyde compounds such as Z-11-hexadecenal, Z-9-tetradecenal and the like, since the method of pest control with a sex pheromone is usually performed by keeping a dispenser filled with the sex pheromone compound in the open field from which the sex pheromone is sustainedly released or emitted into the air to attract the insects a particular sex. When the aldehyde compound as the sex pheromone is oxidized under the influence of ultraviolet or converted to the trimer, the activity of the sex pheromone is naturally lost correspondingly.

Despite the above described demand in the modern pest-control technology, no effective method is known in the prior art for the stabilization of aliphatic higher aldehyde compounds.

SUMMARY OF THE INVENTION

An object of the present invention is to provide a novel method for the stabilization of an aliphatic higher aldehyde compound on prolonged storage by reducing the rate of oxidation thereof into a carboxylic acid and the rate of trimer formation.

Particularly, the object of the present invention is to provide a method for the stabilization of an aliphatic higher aldehyde compound having from 10 to 20 carbon atoms in a molecule.

More particularly, the object of the present invention is to provide a method for the stabilization of Z-11-hexadecenal and Z-9-tetradecenal having an activity as a sex pheromone of some noxious insects.

Thus, the method of the present invention for the stabilization of an aliphatic higher aldehyde compound comprises admixing the aldehyde compound with a stabilizer compound selected from the group consisting of tertiary amine compounds, salicylic acid compounds, benzophenone compounds, benzotriazole compounds and cyanoacrylate compounds in an amount of 0.01 to 10% by weight of the aldehyde compound.

It is sometimes synergistically effective to add an antioxidant to the aldehyde compound in combination with the above mentioned stabilizer compound.

DETAILED DESCRIPTION OF THE PREFERRED EMBODIMENTS

The compounds belonging to the first class of the stabilizer compounds used in the inventive method are tertiary amine compounds which may act as an acid acceptor or a neutralizing agent of the carboxylic acid formed by the oxidation of the aldehyde compound contributing to the prevention of the autoxidation. Furthermore, the addition of a tertiary amine compound to the aldehyde compound is effective to reduce the rate of the trimer formation since the trimer formation is accelerated by the presence of a carboxylic acid, which may be the product of the oxidation reaction of the aldehyde, or a mineral acid.

The particularly effective tertiary amine compounds in the inventive method are exemplified by triethylamine, pyridine, quinoline, nicotinic acid amide, tocopherol nicotinate and the like.

It should be noted that primary amine compounds and secondary amine compounds also have an activity as an acid acceptor or a neutralizing agent of acid but these amine compounds cannot be used in place of the tertiary amine compounds in the inventive method since the primary and secondary amines may react with the aldehyde compound to produce a different impurity compound or to be lost by such a reaction.

The compounds belonging to the other classes of the stabilizer compounds are mostly known as an ultraviolet absorber. Therefore, the compound dissolved in the aldehyde compound effectively absorbs the ultraviolet light to reduce the energy of light otherwise transferred to the aldehyde compound so that the photo-induced oxidation of the aldehyde compound can be prevented.

The salicylic acid compounds are exemplified by phenyl salicylate, p-tert-butylphenyl salicylate and the like, the benzophenone compounds are exemplified by 2,4-dihydroxybenzophenone, 2-hydroxy-4-octyloxy benzophenone and the like, the benzotriazole compounds are exemplified by 2-(2'-hydroxy-5'-methylphenyl)benzotriazole, 2-(2'-hydroxy-3'-tert-butyl-5'-methylphenyl)benzotriazole and the like and the cyanoacrylate compounds are exemplified by ethyl 2-cyano-3,3'-diphenyl acrylate, 2-ethylhexyl-2-cyano-3,3'-diphenyl acrylate and the like. These compounds as well as the tertiary amine compounds may be used either singly or as a combination of two kinds or more according to need. In particular, the combined use of a tertiary amine compound and an ultraviolet absorber compound is sometimes effective synergistically.

The amount of the above described stabilizer compound added to the aliphatic higher aldehyde compound is in the range from 0.01 to 10% by weight based on the aldehyde compound because an amount thereof smaller than 0.01% by weight is almost ineffective while an amount in excess of 10% by weight has no particular additional advantage in respect of the stabilization.

It is optional that the above described stabilizer compound is added to the aldehyde compound in combination with a conventional antioxidant. Suitable antioxidants are exemplified by p-hydroxy anisole, butyl hydroxy anisole, di-tert-butyl-p-cresol, di-tert-butyl resorcine, hydroquinone, di-tert-butyl hydroquinone, tocopherol and the like. When an antioxidant is used in combination with the stabilizer compound, the amount of the antioxidant should be in the range from 0.01 to 5% by weight based on the aldehyde compound. In particular, it is preferable that the total amount of the stabilizer compound and the antioxidant does not exceed 10% by weight.

In the following, the inventive method is described in more detail by way of examples, in which the effectiveness of the inventive method is demonstrated by the determination of the amounts of the carboxylic acid and the trimer formed by the reactions expressed by the reaction equations (I) and (II) given before or by the determination of the residual amount of the aldehyde compound left unchanged by the oxidation reaction or the trimer formation.

EXAMPLE 1

Z-11-Hexadecenal was admixed with a tertiary amine compound shown in Table 1 below in an amount also indicated in the table per 100 g of the above aldehyde compound together with or without an antioxidant and 150 ml of the mixture were taken in a glass vessel and kept standing for 60 days in a thermostat controlled at 30° C. After the lapse of the above mentioned days, the mixture was analyzed for the concentrations of the carboxylic acid and the trimer formed from the aldehyde compound to give the results shown in Table 1.

TABLE 1

| Experiment No. | tert-Amine (amount added, %) | Antioxidant (amount added, %) | Yield of carboxylic acid, % | Yield of trimer, % |
|---|---|---|---|---|
| 1 | None | None | 12.3 | 25.8 |
| 2 | Quinoline (0.1) | None | 1.2 | 0.8 |
| 3 | Tocopherol nicotinate (0.2) | None | 0.8 | 0.7 |
| 4 | Quinoline (0.1) | BHT (0.1) | 0.8 | 0.7 |
| 5 | Pyridine (0.1) | Hydroquinone (0.05) | 0.9 | 0.7 |
| 6 | None | BHT (0.1) | 1.5 | 10.4 |
| 7 | Diphenylamine (0.1) | BHA (0.1) | 1.3 | 8.4 |
| 8 | Triethylamine (0.05) | BHT (0.1) | 1.2 | 2.8 |

BHA: Butyl hydroxyanisole
BHT: Di-tert-butyl-p-cresol

EXAMPLE 2

Z-11-Hexadecenal was admixed with one or two of the stabilizer compounds shown in Table 2 below in amounts also shown in the same table per 30 g of the aldehyde compound together with or without an antioxidant. A capillary tube of a high-density polyethylene having an inner diameter of 0.8 mm, an outer diameter of 1.6 mm and a length of 200 mm was filled with one of the thus prepared mixtures and kept standing for 8 days with the ends sealed. After lapse of 8 days, the mixture in the capillary tube was taken out and subjected to the gas chromatographic analysis to determine the residual content of the Z-11-hexadecenal in % by the internal standard method. The results were as shown in the table. Experiments No. 9 and No. 13 were undertaken for comparative purpose with the aldehyde compound as such and the aldehyde compound admixed with an antioxidant alone, respectively.

TABLE 2

| Experiment No. | Additives Compound | Amount added, g | Residual effective compound, % |
|---|---|---|---|
| 9 | None | — | 31 |
| 10 | Compound I | 0.6 | 72 |
| 11 | Compound I | 0.6 | 84 |
|    | Quinoline | 0.03 | |
| 12 | Compound I | 0.6 | 88 |
|    | Quinoline | 0.03 | |
|    | BHT | 0.6 | |
| 13 | BHT | 0.6 | 48 |
| 14 | Compound II | 0.6 | 70 |
|    | Tocopherol nicotinate | 0.03 | |
|    | Hydroquinone | 0.06 | |

Compound I: 2-Hydroxy-4-octyloxybenzophenone
Compound II: 2-(2'-Hydroxy-3'-tert-butyl-5'-methylphenyl) benzotriazole
BHT: Di-tert-butyl-p-cresol

What is claimed is:

1. A method for the stabilization of an aliphatic higher aldehyde compound having from 10 to 20 carbon atoms in a molecule which comprises admixing the aldehyde compound with a stabilizing effective amount of a compound selected from the group consisting of triethylamine, pyridine, quinoline, nicotinic acid amide, tocopherol nicotinate, phenyl salicylate, p-tert-butylphenyl salicylate, 2,4-dihydroxybenzophenone, 2-hydroxy-4-octyloxy benzophenone, 2-(2'-hydroxy-5'-methylphenyl)benzotriazole, 2-(2'-hydroxy-3'-tert-butyl-5'-methylphenyl)benzotriazole, ethyl 2-cyano-3,3'-diphenyl acrylate and 2-ethylhexyl-2-cyano-3,3'-diphenyl acrylate.

2. The method as claimed in claim 1 wherein the amount of the stabilizer compound is in the range from 0.01 to 10% by weight based on the aldehyde compound.

3. The method of claim 1 wherein the stabilizer compound is a combination of a tertiary amine compound selected from the group consisting of triethylamine, pyridine, quinoline, nicotinic acid amide, and tocopherol nicotinate, and another compound selected from the group consisting of phenyl salicylate, p-tert-butylphenyl salicylate, 2,4-di-hydroxybenzophenone, 2-hydroxy-4-octyloxy benzophenone, 2-(2'-hydroxy-5'-methylphenyl)benzotriazole, 2-(2'-hydroxy-3'-tert-butyl-5'-methylphenyl)benzotriazole, ethyl 2-cyano-3,3'-diphenyl acrylate and 2-ethylhexyl-2-cyano-3,3'-diphenyl acrylate.

4. The method of claim 1 wherein the aldehyde compound is further admixed with an antioxidizing effective amount of an antioxidant.

5. The method of claim 1 wherein the aldehyde compound is selected from the group consisting of Z-11-hexadecenal and Z-9-tetradecenal.

6. The method as claimed in claim 4 wherein the amount of the antioxidant is in the range from 0.01 to 5% by weight based on the aldehyde compound.

7. The method as claimed in claim 4 wherein the antioxidant is selected from the group consisting of p-hydroxy anisole, butyl hyroxy anisole, di-tert-butyl-p-cresol, di-tert-butyl resorcine, hydroquinone, di-tert-butyl hydroquinone and tocopherol.

* * * * *